US012802183B2

(12) United States Patent
Song

(10) Patent No.: US 12,802,183 B2
(45) Date of Patent: Nov. 17, 2026

(54) IMAGE CORRECTION METHOD AND APPARATUS BASED ON FPGA, AND DEVICE AND MEDIUM

(71) Applicant: Shenzhen Beacon Display Technology Co., Ltd., Shenzhen (CN)

(72) Inventor: Ziyang Song, Shenzhen (CN)

(73) Assignee: Shenzhen Beacon Display Technology Co., Ltd., Shenzhen (CN)

( * ) Notice: Subject to any disclaimer, the term of this patent is extended or adjusted under 35 U.S.C. 154(b) by 190 days.

(21) Appl. No.: 18/855,318

(22) PCT Filed: Jan. 9, 2023

(86) PCT No.: PCT/CN2023/071254
§ 371 (c)(1),
(2) Date: Oct. 9, 2024

(87) PCT Pub. No.: WO2024/138793
PCT Pub. Date: Jul. 4, 2024

(65) Prior Publication Data
US 2025/0328999 A1 Oct. 23, 2025

(30) Foreign Application Priority Data
Dec. 28, 2022 (CN) ......................... 202211697007.4

(51) Int. Cl.
*G06T 5/80* (2024.01)
*G06T 5/92* (2024.01)
(Continued)

(52) U.S. Cl.
CPC .................. *G06T 5/80* (2024.01); *G06T 5/92* (2024.01); *G06V 10/56* (2022.01); *G06V 10/60* (2022.01);
(Continued)

(58) Field of Classification Search
CPC ... G06T 5/80; G06T 5/92; G06T 2207/10024; G06T 5/90; G06T 7/0012; G06T 7/90;
(Continued)

(56) References Cited

U.S. PATENT DOCUMENTS

2008/0089572 A1* 4/2008 Yamano ................. A61B 6/461
348/E9.054
2012/0113132 A1* 5/2012 Jiang ...................... G09G 5/028
345/600
(Continued)

FOREIGN PATENT DOCUMENTS

CN 104205202 A * 12/2014 ........... G09G 3/3426
CN 104737222 A * 6/2015 ............... G09G 5/06
(Continued)

*Primary Examiner* — Jose L Couso

(57) ABSTRACT

Provided are an image correction method and apparatus based on an FPGA, and a device and a medium, which can identify color grayscale attributes of a video by using modules of the FPGA and by taking pixel points as units, so as to solve the problem of area identification being inaccurate or an area size being limited. Color pixel points are separated into brightness parts and chromatic aberration parts, and according to a mapping relationship, the transition of a color and grayscale transition part is made uniform; chromatic aberration is used for performing brightness compensation for a GAMMA curve; and the color part keeps the characteristics of the GAMMA curve, and monochromatic grayscale pixel points are corrected by means of the DICOM curve, and adaptive correction of color grayscale video images is thus achieved on the basis of an FPGA.

20 Claims, 3 Drawing Sheets

(51) Int. Cl.
*G06V 10/56* (2022.01)
*G06V 10/60* (2022.01)
*G16H 30/20* (2018.01)
*H04N 1/60* (2006.01)

(52) U.S. Cl.
CPC ........... *G16H 30/20* (2018.01); *H04N 1/6019* (2013.01); *G06T 2207/10024* (2013.01)

(58) Field of Classification Search
CPC ............. G06T 5/40; G06T 2207/10081; G06T 2207/30004; G06T 2210/41; G06T 3/4046; G06T 5/60; G06T 9/002; G06T 2207/20076; G06T 2207/20081; G06T 2207/20084; G06T 2211/441; G06V 10/56; G06V 10/60; G06V 10/25; G06V 2201/03; G06V 10/80; G06V 10/454; G06V 10/54; G06V 10/70; G06V 10/764; G06V 10/774; G06V 10/82; G06V 10/84; G06V 20/41; G06V 30/18057; G06V 20/698; G06V 30/19173; G06V 30/194; G16H 30/20; G16H 30/40; G16H 50/20; G16H 20/40; G16H 50/50; H04N 1/6019; H04N 5/202; H04N 9/77; H04N 25/44; H04N 1/40012; H04N 1/6022; H04N 2201/0079; G09G 5/02; G09G 5/06; G09G 5/10; G09G 2320/0666; G09G 2320/04; G09G 2320/0626; G09G 2340/06; G09G 2360/04; G09G 2380/08; G09G 5/005; G09G 5/028; Y02D 10/00; A61B 5/0077; A61B 6/03; A61B 6/032; G06N 3/02; G06N 3/08–088; G06N 3/04; G06N 3/0445; G06N 3/0454; G06N 3/0464; G06N 3/0475; G06N 3/4046; G06N 3/4053; G06N 3/049; G06N 3/0499; G06N 7/00; G06N 7/01; G06N 20/00; G06K 7/1482; G06F 18/213; G06F 18/214; G06F 18/22; G06F 18/241; G06F 18/24; G06F 18/2411; G06F 18/2415; G06F 18/253; G06F 30/27; G05B 2219/25255; G05B 2219/41054; Y10S 128/925
See application file for complete search history.

(56) References Cited

U.S. PATENT DOCUMENTS

| | | | | |
|---|---|---|---|---|
| 2012/0250956 | A1* | 10/2012 | Bocirnea | H04N 19/48<br>382/128 |
| 2013/0259365 | A1* | 10/2013 | Suzuki | G06T 5/90<br>382/164 |
| 2019/0027082 | A1* | 1/2019 | Van Belle | G09G 3/2003 |
| 2026/0179518 | A1* | 6/2026 | Carbonara | G02B 5/201 |

FOREIGN PATENT DOCUMENTS

| | | | | | |
|---|---|---|---|---|---|
| CN | 107408373 | A | * | 11/2017 | G09G 5/14 |
| CN | 108717847 | A | * | 10/2018 | G09G 5/10 |
| CN | 108877735 | A | * | 11/2018 | G09G 5/10 |
| CN | 111951745 | A | * | 11/2020 | G09G 5/10 |

* cited by examiner

IMAGE CORRECTION METHOD AND APPARATUS BASED ON FPGA, AND DEVICE AND MEDIUM

TECHNICAL FIELD

The present application relates to the technical field of image processing, and more particularly to an image correction method and an apparatus based on an FPGA, and a device and a medium.

BACKGROUND ART

With the continuous development of digital image technology and display technology, the existing display products have been developed to integrate high resolution, wide color gamut and high frame rate, and the display is also developing towards intelligence and multifunction. However, in the fields such as medical display, the medical images involved include both diagnostic grayscale images and surgical color images, and in order to meet the display characteristics, grayscale images and color images often need different correction methods, such as Digital Imaging and Communications in Medicine (DICOM) correction curve for grayscale images and GAMMA correction curve for color images.

In view of the above, hospitals may need to have both a grayscale display and a color display in order to meet the correction requirements for different displayed images, which not only increases complexity for connecting the equipment and cable, but also affects aesthetics. In addition, due to the high resolution and large display size of the Liquid Crystal Display (LCD) display panel currently used on the market, more and more medical display manufacturers start to study the simultaneous display of color and grayscale images on a single high-resolution display. A display Scaler chip can generally perform different correction methods for different input signals, as shown in FIG. 1, DICOM curve correction performed for grayscale image input such as Computed Tomography (CT) and Magnetic Resonance Imaging (MRI), and GAMMA2.2 curve correction is performed for endoscopic surgery system image input. However, the above methods can only use different correction curves to meet the display requirements by manually selecting different inputs.

Some medical display manufacturers are studying intelligent color grayscale adaptive correction methods. For example, first, the color grayscale attribute of image is determined; if the determination result is grayscale pixel, the DICOM curve is used for correction; if the determination result is color pixel, the GAMMA2.2 curve is used for correction. This method is convenient to implement, and can be used in the scene where grayscale and color image are separated into separate areas. However, for the picture where grayscale and color pixels are randomly distributed, there is a problem of abnormal display. Due to excessive brightness gradient of the DICOM curve and the GAMMA curve at the same grayscale, it will lead to the problems of noisy points, color blocks or color spots in adjacent pixels of color grayscale. As shown in FIG. 2, a small square represents a pixel point, a grayscale point is represented by Y, and a color point is represented by C; when the RGB component of the grayscale point is close to the RGB component of the color point (the components are close but belong to color pixels and grayscale pixels respectively), a problem of noisy points may occur due to the use of different correction curves.

In addition, grayscale areas and color areas can be automatically identified, and then the DICOM curve correction and the GAMMA2.2 curve correction are applied to different areas. The method cannot predict the data of the displayed image itself, so there are problems of inaccurate area determination or limitation of area size. The application scene is also relatively single, which can only be applied to the regular grayscale area and color area. As the brightness gradient of the DICOM curve and the GAMMA2.2 curve is too large, there will be display abnormality at the area transition, and when a single image is displayed on full screen, there will also be color block, spot and other problems. As shown in FIG. 3, for different grayscale and color areas, a full screen display of the same image may cause problems of noisy points or spots where the grayscale area is adjacent to the color area.

SUMMARY OF THE INVENTION

In view of the above, it would be desirable to provide an image correction method and an apparatus based on an FPGA, and a device and a medium capable of simultaneously displaying grayscale and color images on a single display while preserving the display characteristics of the respective images.

An image correction method based on an FPGA, the image correction method based on an FPGA including:

- being applied to an image correction system based on an FPGA, where the image correction system based on an FPGA includes a color grayscale pixel identification model, a brightness and chromatic aberration separation module, a GAMMA mapping processing module, a GAMMA chromatic aberration compensation module, a DICOM mapping processing module, a timing alignment module and a DICOM curve correction module, and the image correction method based on an FPGA includes:
- when a video to be processed is received, identifying, by the color grayscale pixel identification model, the pixel type of the video to be processed;
- when the pixel type is a grayscale pixel, after a timing alignment module executes delay processing, correcting, by a DICOM curve correction module, the video to be processed, so as to obtain a video to be output and then outputs same;
- when the pixel type is a color pixel, performing separation, by a brightness and chromatic aberration separation module, on the video to be processed, so as to obtain initial brightness and initial chromatic aberration of the video to be processed; performing mapping processing, by a GAMMA mapping processing module, on the basis of a preconfigured mapping relationship and the initial brightness, so as to obtain a first RGB, of the video to be processed, in the GAMMA curve; compensating, by a GAMMA chromatic aberration compensation module, for the first RGB on the basis of the initial chromatic aberration, so as to obtain a second RGB; performing mapping processing, by a DICOM mapping processing module, on the basis of the mapping relationship and the second RGB, so as to obtain a third RGB, of the video to be processed, in the DICOM curve; and performing, by a DICOM curve correction module, correction on the basis of the third RGB, so as to obtain a video to be output and then outputs same According to a preferred embodiment of the present application, the identifying, by a color grayscale pixel identification model, the pixel type of the video to be processed includes:

acquiring an R value, a G value and a B value of each pixel point in the video to be processed;

acquiring a preconfigured component difference threshold;

calculating a component difference between the R value and the G value, a component difference between the G value and the B value and a component difference between the R value and the B value of each pixel point, so as to obtain a component difference corresponding to each pixel point;

when the component difference of each pixel point in the video to be processed is less than or equal to the component difference threshold, determining the video to be processed as the grayscale pixel; or when the component difference of each pixel point in the video to be processed is not all less than or equal to the component difference threshold, determining the video to be processed as the color pixel.

According to a preferred embodiment of the present application, the identifying, by a color grayscale pixel identification model, the pixel type of the video to be processed includes: converting the video to be processed from an RGB color space to a YCbCr color space;

when each pixel point in the video to be processed satisfies Cb=Cr=0, determining the video to be processed as the grayscale pixel; or when each pixel point in the video to be processed does not satisfy Cb=Cr=0, determining that the video to be processed is the color pixel.

According to a preferred embodiment of the present application, the mapping relationship is:

$$D(x) = \frac{n}{m} G(x) + b;$$

where D(x) represents a correction function corresponding to the DICOM curve; G (x) represents a correction function corresponding to the GAMMA curve;

$$\frac{n}{m}$$

represents a mapping factor, the value range of $$\frac{n}{m}$$

is [0.9, 1.1], and n and m are positive integers; b represents a mapping brightness offset amount;

the GAMMA mapping processing module performs mapping processing based on a preconfigured mapping relationship and the initial brightness, so as to obtain a first RGB of the video to be processed in the GAMMA curve includes:

determining an RGB value corresponding to the initial brightness in the DICOM curve; and inputting an RGB value corresponding to the initial brightness in the DICOM curve into the mapping relationship for mapping processing, so as to obtain the first RGB of the video to be processed in the GAMMA curve.

According to a preferred embodiment of the present application, the compensating, by the GAMMA chromatic aberration compensation module, the first RGB based on the initial chromatic aberration, so as to obtain a second RGB includes:

compensating the first RGB based on the initial chromatic aberration using the following formula:

$$\begin{bmatrix} R2 \\ G2 \\ B2 \end{bmatrix} = \begin{bmatrix} k1 & 0 & 0 \\ 0 & k2 & 0 \\ 0 & 0 & k3 \end{bmatrix} \times \begin{bmatrix} Rca \\ Gca \\ Bca \end{bmatrix} + \begin{bmatrix} R1 \\ G1 \\ B1 \end{bmatrix}$$

where $$\begin{bmatrix} R2 \\ G2 \\ B2 \end{bmatrix}$$

represents an RGB matrix corresponding to the second RGB, and $$\begin{bmatrix} Rca \\ Gca \\ Bca \end{bmatrix}$$

represents an RGB matrix corresponding to the initial chromatic aberration;

$$\begin{bmatrix} R1 \\ G1 \\ B1 \end{bmatrix}$$

represents an RGB matrix corresponding to the first RGB, $$\begin{bmatrix} k1 & 0 & 0 \\ 0 & k2 & 0 \\ 0 & 0 & k3 \end{bmatrix}$$

represents a chromatic aberration compensation coefficient matrix, k1, k2, and k3 respectively represent a chromatic aberration compensation coefficient, and the value ranges of k1, k2, and k3 are [0, 2].

According to a preferred embodiment of the present application, the DICOM curve correction module performing correction based on the third RGB, so as to obtain the video to be output includes:

acquiring an LUT display look-up table; and correcting the third RGB based on the LUT display look-up table, so as to obtain the video to be output.

According to a preferred embodiment of the present application, the outputting the video to be output includes:

transmitting the video to be output to a display apparatus connected to the image correction system based on an FPGA.

An image correction apparatus based on an FPGA is operated for an image correction system based on an FPGA, where the image correction system based on an FPGA includes a color grayscale pixel identification model, a brightness and chromatic aberration separation module, a GAMMA mapping processing module, a GAMMA chromatic aberration compensation module, a DICOM mapping processing module, a timing alignment module and a DICOM curve correction module, and the image correction apparatus based on an FPGA includes:

the color grayscale pixel identification model configured to identify the pixel type of the video to be processed when the video to be processed is received;

the DICOM curve correction module configured to, when the pixel type is a grayscale pixel, after the timing alignment module executes delay processing, correct the video to be processed, so as to obtain a video to be output and output the video to be output;

the brightness and chromatic aberration separation module configured to, when the pixel type is a color pixel, separate the video to be processed, so as to obtain an initial brightness and an initial chromatic aberration of the video to be processed;

the GAMMA mapping processing module configured to perform mapping processing based on a preconfigured mapping relationship and the initial brightness, so as to obtain a first RGB of the video to be processed in the GAMMA curve;

the GAMMA chromatic aberration compensation module configured to compensating the first RGB based on the initial chromatic aberration, so as to obtain a second RGB;

the DICOM mapping processing module configured to perform mapping processing on the basis of the mapping relationship and the second RGB, so as to obtain a third RGB of the video to be processed in the DICOM curve; and the DICOM curve correction module further configured to perform correction based on the third RGB, so as to obtain the video to be output and output the video to be output.

A computer device including:

memory storing at least one instruction; and a processor executing instructions stored in the memory to implement the image correction method based on an FPGA.

A computer-readable storage medium, where the computer-readable storage medium has stored therein at least one instruction for execution by a processor in a computer device to implement the image correction method based on an FPGA.

It can be seen from the above-mentioned technical solution that the present application can identify color grayscale attributes of a video by using functional modules of the FPGA and by taking pixel points as units, so as to solve the problem of area identification being inaccurate or an area size being limited in sub-region identification, thereby meeting display application of images in any scene. Color pixel points are further separated into brightness parts and chromatic aberration parts, and according to a mapping relationship between the DICOM curve and the GAMMA curve, the transition of a color and grayscale transition part is made uniform; chromatic aberration is further used for performing brightness compensation for a GAMMA curve, such that the grayscale brightness of the GAMMA curve of a color part is basically consistent with that of a DICOM curve, so as to reduce a brightness gradient between different image grayscales, thereby solving the problems of noisy points, color blocks and color spots, etc. being present in a transition area during image display; and at the same time, the color part keeps the characteristics of the GAMMA curve, and monochromatic grayscale pixel points are corrected by means of the DICOM curve, and adaptive correction of color grayscale video images is thus achieved on the basis of an FPGA.

DETAILED DESCRIPTION OF THE INVENTION

In order that the objects, aspects, and advantages of the present application will become apparent, a more particular description of the present application will be rendered by reference to specific embodiments thereof which are illustrated in the appended drawings.

Figure 1:
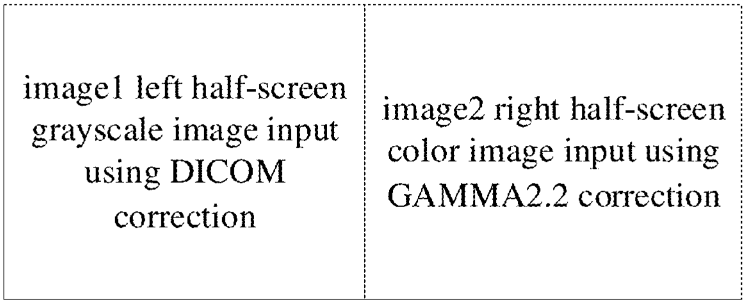
FIG. 1 is a schematic diagram showing different corrections for different inputs by a Scaler chip according to the present application.
Figure 2:
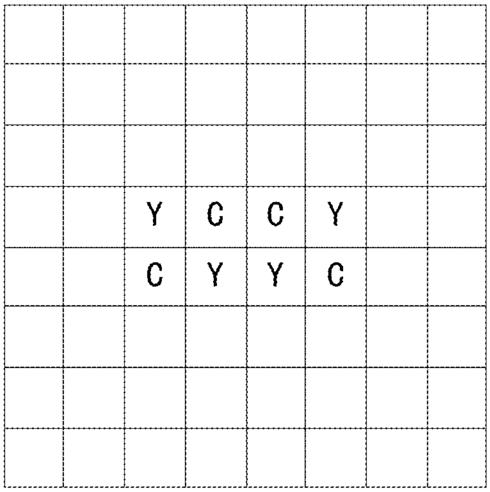
FIG. 2 is a schematic diagram showing identifying color pixels and grayscale pixels according to the present application.
Figure 3:
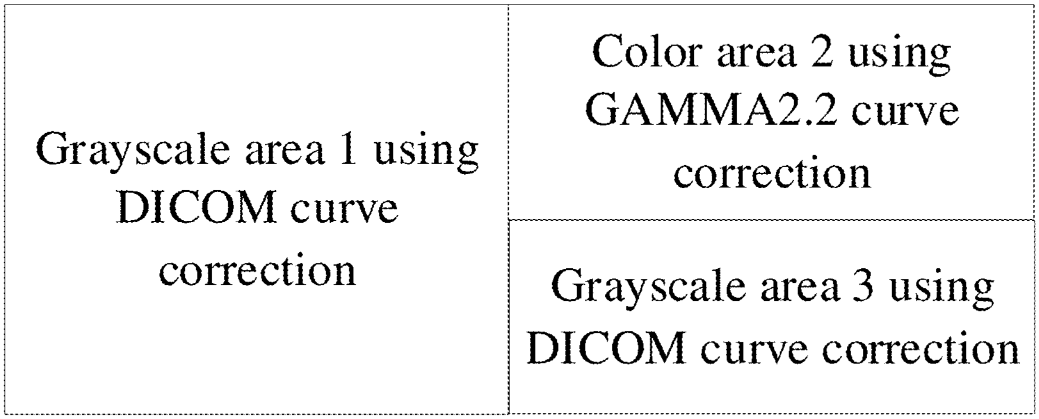
FIG. 3 is a schematic diagram showing color grayscale correction based on area identification according to the present application.
Figure 4:
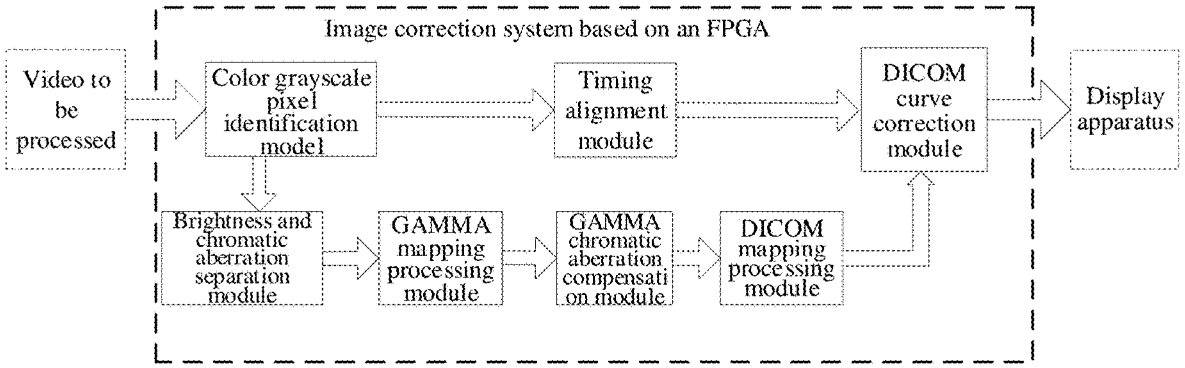
FIG. 4 is a schematic diagram showing an application environment of an image correction method based on an FPGA according to the present application.

FIG. 4 shows a schematic diagram showing an application environment of an image correction method based on an FPGA according to the present application. When a video to be processed is input to the Field Programmable Gate Array (FPGA)-based image correction system, the video is processed successively by a color grayscale pixel identification model, a brightness and chromatic aberration separation module, a GAMMA mapping processing module, a GAMMA chromatic aberration compensation module, a Digital Imaging and Communications in Medicine (DICOM) mapping processing module, a timing alignment module and a DICOM curve correction module in the image correction system based on the FPGA, and finally the correction result is output to a display apparatus for display.

Figure 5:
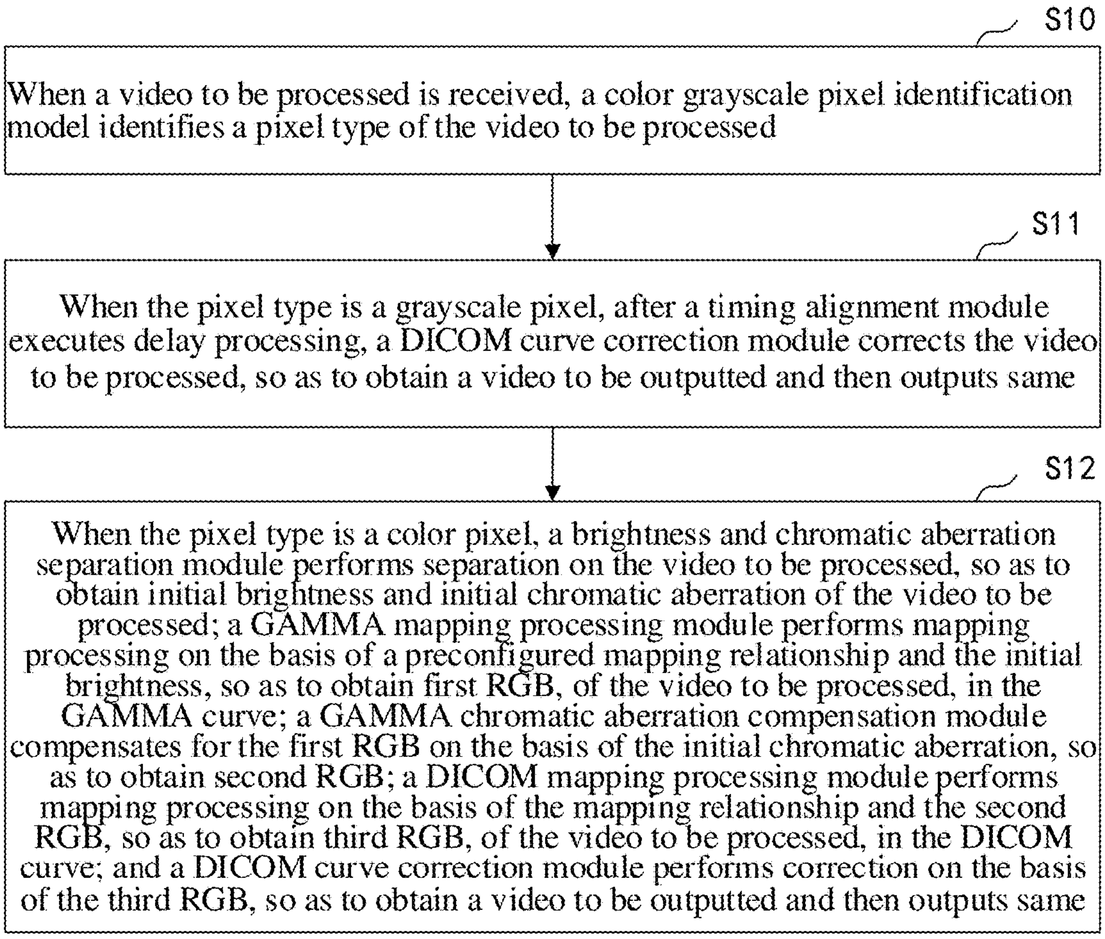
FIG. 5 is a flow chart showing a preferred embodiment of an image correction method based on an FPGA according to the present application.

FIG. 5 shows a flow chart showing a preferred embodiment of an image correction method based on an FPGA according to the present application. The order of the steps in the flow chart may be varied and certain steps may be omitted according to different requirements.

The image correction method based on an FPGA is applied to one or more computer devices, which is a device capable of automatic numerical calculation and/or information processing according to pre-set or stored instructions, whose hardware includes but is not limited to microprocessor, Application Specific Integrated Circuit (ASIC), Field-Programmable Gate Array (FPGA), Digital Signal Processor (DSP), embedded device, etc.

The computer device may be any electronic product that can interact with a user, such as a personal computer, a tablet, a smartphone, a Personal Digital Assistant (PDA), a game player, an Internet Protocol Television (IPTV), a smart wearable device, etc.

The computer device may further include a network device and/or a user device. The network device includes, but is not limited to, a single network server, a server group composed of multiple network servers, or a cloud composed of a large number of hosts or network servers based on cloud computing (Cloud Computing).

The server can be an independent server, and can also be a cloud server providing basic cloud computing services, such as a cloud service, a cloud database, cloud computing, a cloud function, cloud storage, a network service, cloud communication, a middleware service, a domain name service, a security service, a Content Delivery Network (CDN), and a large data and artificial intelligence platform.

An Artificial Intelligence (AI) is a theory, method, technology and application system that uses a digital computer or digital computer-controlled machine to simulate, extend and expand human intelligence, perceive the environment, acquire knowledge and use the knowledge, so as to obtain the best results.

The basic technologies of artificial intelligence generally include such technologies as sensor, special artificial intelligence chip, cloud computing, distributed storage, large data processing technology, operation/interaction system, electromechanical integration, etc. Artificial intelligence software technology mainly includes computer vision technology, robot technology, biological identification technology, speech processing technology, natural language processing technology and machine learning/in-depth learning.

The network in which the computer device is located includes, but is not limited to, the Internet, a wide area network, a metropolitan area network, a local area network, a Virtual Private Network (VPN), etc.

The present embodiment is applied to a Field Programmable Gate Array (FPGA)-based image correction system, where the image correction system based on an FPGA includes a color grayscale pixel identification model, a brightness and chromatic aberration separation module, a GAMMA mapping processing module, a GAMMA chromatic aberration compensation module, a Digital Imaging and Communications in Medicine (DICOM) mapping processing module, a timing alignment module and a DICOM curve correction module, and the image correction method based on an FPGA includes:

S10 When a video to be processed is received, identify, by the color grayscale pixel identification model, the pixel type of the video to be processed.

The video to be processed can be grayscale images such as Computed Tomography (CT) and Magnetic Resonance Imaging (MRI), and can also be color imaging of endoscopic surgery system, etc.

The video to be processed may also be first processed by a Scaler image processing module. The Scaler image processing module mainly realizes multi-path video input, multi-picture window layout processing and menu control functions, etc. For example: the video processed by the Scaler image processing module can be input to the image correction system based on an FPGA, and the color grayscale adaptive correction and split-screen GAMMA correction functions are completed in the image correction system based on an FPGA, and finally the correction result is output to a display apparatus to complete the display and presentation of a video image.

FPGA is a hardware programmable logic device, and the image processing implemented thereby is a pure hardware processing mode, and the programmability thereof provides a strong scalability, and using the FPGA architecture can provide more differentiated image processing functions.

In the present embodiment, the identifying, by a color grayscale pixel identification model, the pixel type of the video to be processed includes:

acquiring an R (Red) value, a G (Green) value and a B (Blue) value of each pixel point in the video to be processed;

acquiring a preconfigured component difference threshold;

calculating a component difference between the R value and the G value, a component difference between the G value and the B value and a component difference between the R value and the B value of each pixel point, so as to obtain a component difference corresponding to each pixel point;

when the component difference of each pixel point in the video to be processed is less than or equal to the component difference threshold, determining the video to be processed as the grayscale pixel; or when the component difference of each pixel point in the video to be processed is not all less than or equal to the component difference threshold, determining the video to be processed as the color pixel.

In the present embodiment, the identifying, by a color grayscale pixel identification model, the pixel type of the video to be processed includes:

converting the video to be processed from an RGB color space to a YCbCr color space;

when each pixel point in the video to be processed satisfies Cb=Cr=0, determining the video to be processed as the grayscale pixel; or when each pixel point in the video to be processed does not satisfy Cb=Cr=0, determining that the video to be processed is the color pixel.

The present embodiment uses the color grayscale identification method of pix by pix to complete color grayscale pixel point identification in the unit of pixel points, and solves the problem of inaccurate area identification or limitation of area size in sub-area identification, and can satisfy the display application of any scene image.

S11 When the pixel type is a grayscale pixel, after a timing alignment module executes delay processing, correct by a DICOM curve correction module, the video to be processed, so as to obtain a video to be output and then outputs same For example: a pixel processed by the color grayscale pixel identification model, and if it is a grayscale pixel point, the timing alignment module processes a pipeline delay, and the number of delays is synchronized with the pipeline delay processed by the color pixel point, and is output to a post-stage processing module.

S12 When the pixel type is a color pixel, perform separation, by a brightness and chromatic aberration separation module, on the video to be processed, so as to obtain initial brightness and initial chromatic aberration of the video to be processed; perform mapping processing, by a GAMMA mapping processing module, on the basis of a preconfigured mapping relationship and the initial brightness, so as to obtain a first RGB, of the video to be processed, in the GAMMA curve; compensate, by a GAMMA chromatic aberration compensation module, for the first RGB on the basis of the initial chromatic aberration, so as to obtain a second RGB; perform mapping processing, by a DICOM mapping processing module, on the basis of the mapping relationship and the second RGB, so as to obtain a third RGB, of the video to be processed, in the DICOM curve; and perform, by a DICOM curve correction module, correction on the basis of the third RGB, so as to obtain a video to be output and then outputs same In the present embodiment, if it is a color pixel point, the brightness and chromatic aberration separation module separates the color pixel point into brightness and chromatic aberration parts, where the brightness is represented by L, and the chromatic aberration is represented by Rca, Gca and Bca respectively, and outputs same to a post-stage processing module.

In the present embodiment, the mapping relationship is:

$$D(x)=\frac{n}{m}G(x)+b;$$

where D(x) represents a correction function corresponding to the DICOM curve; G (x) represents a correction function corresponding to the GAMMA curve;

$$\frac{n}{m}$$

represents a mapping factor, the value range of $$\frac{n}{m}$$

is [0.9, 1.1], and n and m are positive integers; b represents a mapping brightness offset amount.

If the value of $$\frac{n}{m}$$

is too large or too small, the noisy points and color blocks will be caused to different degrees.

Where b is used as the mapping brightness offset amount, when the offset amount is increased, the brightness mapping relationship between the two curves can be corrected, and the range of b can be positive or negative.

When different DICOM and GAMMA curves are used, the above parameters can be used for fine-tuning the effect.

Where the GAMMA curve can include, but is not limited to: GAMMA1.8, GAMMA2.0, GAMMA2.2, GAMMA2.4, GAMMA2.6, etc.;

Where the DICOM curve can include, but is not limited to: DICOM300, DICOM400, DICOM500, DICOM600, DICOM700, etc.

By establishing the mapping relationship between the DICOM curve and the GAMMA curve, the brightness gradient between color pixels and grayscale pixels is reduced, thus the color grayscale transition part is smoother, and the problems of noisy points and color blocks are eliminated.

In the present embodiment, the GAMMA mapping processing module performs mapping processing based on a preconfigured mapping relationship and the initial brightness, so as to obtain a first RGB of the video to be processed in the GAMMA curve includes:

determining an RGB value corresponding to the initial brightness in the DICOM curve; and inputting an RGB value corresponding to the initial brightness in the DICOM curve into the mapping relationship for mapping processing, so as to obtain the first RGB of the video to be processed in the GAMMA curve.

In the present embodiment, the compensating, by the GAMMA chromatic aberration compensation module, the first RGB based on the initial chromatic aberration, so as to obtain a second RGB includes:

compensating the first RGB based on the initial chromatic aberration using the following formula:

$$\begin{bmatrix}R2\\G2\\B2\end{bmatrix}=\begin{bmatrix}k1&0&0\\0&k2&0\\0&0&k3\end{bmatrix}\times\begin{bmatrix}Rca\\Gca\\Bca\end{bmatrix}+\begin{bmatrix}R1\\G1\\B1\end{bmatrix}$$

where $$\begin{bmatrix}R2\\G2\\B2\end{bmatrix}$$

represents an RGB matrix corresponding to the second RGB, and $$\begin{bmatrix}Rca\\Gca\\Bca\end{bmatrix}$$

represents an RGB matrix corresponding to the initial chromatic aberration;

$$\begin{bmatrix}R1\\G1\\B1\end{bmatrix}$$

represents an RGB matrix corresponding to the first RGB, $$\begin{bmatrix}k1&0&0\\0&k2&0\\0&0&k3\end{bmatrix}$$

represents a chromatic aberration compensation coefficient matrix, k1, k2, and k3 respectively represent a chromatic aberration compensation coefficient, and the value ranges of k1, k2, and k3 are [0, 2].

Where k1, k2, and k3 are used as the chromatic aberration compensation coefficient, different values can be taken for different chromatic aberration signals of RGB, k1, k2, and k3 are used for adjusting the chroma effect of color pixel points, which can meet the requirements of different users on chroma effects.

The chroma effects of the color pixel point GAMMA can be preserved by chromatic aberration compensation.

In the present embodiment, the way the DICOM mapping processing module performs mapping processing based on the mapping relationship and the second RGB is equivalent to an inverse process in which the GAMMA mapping processing module performs mapping processing based on a preconfigured mapping relationship and the initial brightness, which will not be described in detail herein.

In the present embodiment, the DICOM curve correction module performing correction based on the third RGB, so as to obtain the video to be output includes:

acquiring a Look-Up-Table (LUT) to display a look-up table;

correcting the third RGB based on the LUT display look-up table, so as to obtain the video to be output.

In the present embodiment, the outputting the video to be output includes:

transmitting the video to be output to a display apparatus connected to the image correction system based on an FPGA.

For example: the display apparatus may be a medical display in the field of color displays, a general display, various display terminals, etc. When the display needs different adaptive correction processing of GAMMA and DICOM for the color grayscale pixels in the same display image, it cannot be completed in a single Scaler chip, only the special function of differentiation can be completed through the hardware programmable features of FPGA. Therefore, the image correction method based on an FPGA in the present embodiment can be used, and then the grayscale and color image can be accurately displayed on a single display at the same time, and the display characteristics of the respective images are retained.

Specifically, the adaptive hybrid GAMMA display method is implemented by using FPGA pure hardware through the color grayscale adaptive correction processing based on an FPGA, which can automatically identify the color pixels and monochrome grayscale pixels in the displayed image. The monochromatic pixels is subjected to a DICOM curve correction processing; after the separation of brightness and chromatic aberration, GAMMA mapping processing, GAMMA chromatic aberration compensation processing, DICOM mapping processing, and finally DICOM curve correction processing can effectively solve the problem of excessive brightness gradient of the DICOM curve and the GAMMA curve at the same grayscale, make the color grayscale image transition part display uniform, while the color part retains the curve characteristics of GAMMA.

It can be seen from the above-mentioned technical solution that the present application can identify color grayscale attributes of a video by using functional modules of the FPGA and by taking pixel points as units, so as to solve the problem of area identification being inaccurate or an area size being limited in sub-region identification, thereby meeting display application of images in any scene. Color pixel points are further separated into brightness parts and chromatic aberration parts, and according to a mapping relationship between the DICOM curve and the GAMMA curve, the transition of a color and grayscale transition part is made uniform; chromatic aberration is further used for performing brightness compensation for a GAMMA curve, such that the grayscale brightness of the GAMMA curve of a color part is basically consistent with that of a DICOM curve, so as to reduce a brightness gradient between different image grayscales, thereby solving the problems of noisy points, color blocks and color spots, etc. being present in a transition area during image display; and at the same time, the color part keeps the characteristics of the GAMMA curve, and monochromatic grayscale pixel points are corrected by means of the DICOM curve, and adaptive correction of color grayscale video images is thus achieved on the basis of an FPGA.

Figure 6:
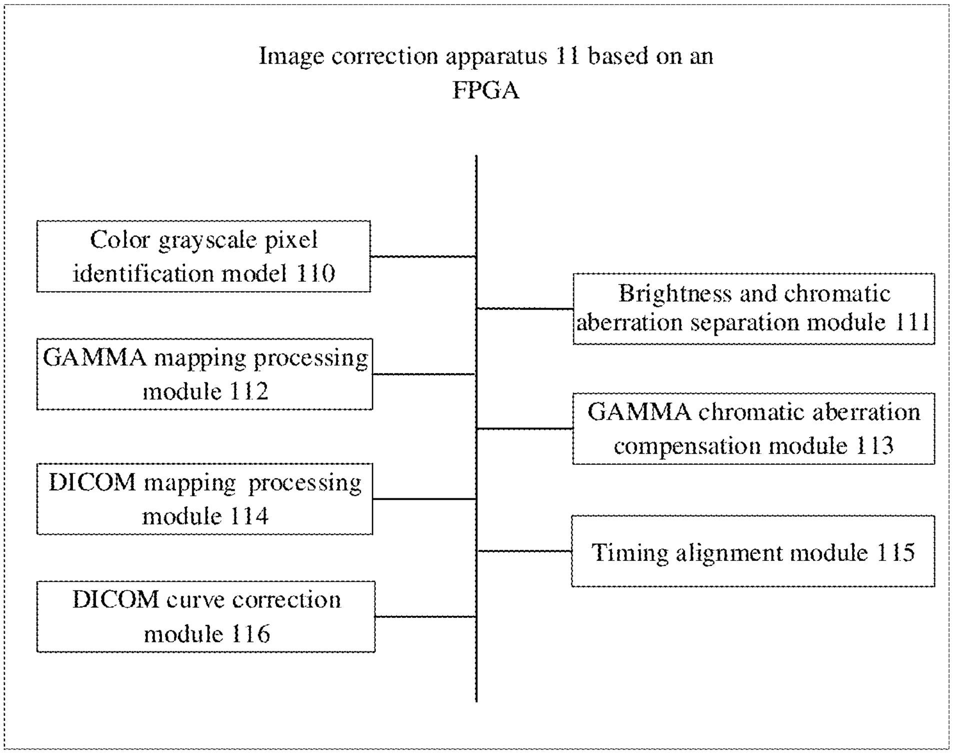
FIG. 6 is a functional block diagram showing a preferred embodiment of an image correction apparatus based on an FPGA according to the present application.

FIG. 6 shows a functional block diagram showing a preferred embodiment of an image correction apparatus based on an FPGA according to the present application. The image correction apparatus 11 based on an FPGA includes a color grayscale pixel identification model 110, a brightness and chromatic aberration separation module 111, a GAMMA mapping processing module 112, a GAMMA chromatic aberration compensation module 113, a DICOM mapping processing module 114, a timing alignment module 115 and a DICOM curve correction module 116. A module/unit as referred to herein refers to a series of computer program segments capable of being executed by a processor and performing fixed functions, and stored in a memory. In the present embodiment, the functions of the respective modules/units will be described in detail in the following embodiments.

The present embodiment is applied to a Field Programmable Gate Array (FPGA)-based image correction system, where the image correction system based on an FPGA includes a color grayscale pixel identification model 110, a brightness and chromatic aberration separation module 111, a GAMMA mapping processing module 112, a GAMMA chromatic aberration compensation module 113, a Digital Imaging and Communications in Medicine (DICOM) mapping processing module 114, a timing alignment module 115 and a DICOM curve correction module 116, and the system includes:

the color grayscale pixel identification model 110 configured to identify the pixel type of the video to be processed when the video to be processed is received.

The video to be processed can be grayscale images such as Computed Tomography (CT) and Magnetic Resonance Imaging (MRI), and can also be color imaging of endoscopic surgery system, etc.

The video to be processed may also be first processed by a Scaler image processing module. The Scaler image processing module mainly realizes multi-path video input, multi-picture window layout processing and menu control functions, etc. For example: the video processed by the Scaler image processing module can be input to the image correction system based on an FPGA, and the color grayscale adaptive correction and split-screen GAMMA correction functions are completed in the image correction system based on an FPGA, and finally the correction result is output to a display apparatus to complete the display and presentation of a video image.

FPGA is a hardware programmable logic device, and the image processing implemented thereby is a pure hardware processing mode, and the programmability thereof provides a strong scalability, and using the FPGA architecture can provide more differentiated image processing functions.

In the present embodiment, the color grayscale pixel identification model 110 identifying the pixel type of the video to be processed includes:

acquiring an R (Red) value, a G (Green) value and a B (Blue) value of each pixel point in the video to be processed;

acquiring a preconfigured component difference threshold;

calculating a component difference between the R value and the G value, a component difference between the G value and the B value and a component difference between the R value and the B value of each pixel point, so as to obtain a component difference corresponding to each pixel point;

when the component difference of each pixel point in the video to be processed is less than or equal to the component difference threshold, determining the video to be processed as the grayscale pixel; or when the component difference of each pixel point in the video to be processed is not all less than or equal to the component difference threshold, determining the video to be processed as the color pixel.

In the present embodiment, the color grayscale pixel identification model 110 identifying the pixel type of the video to be processed includes:

converting the video to be processed from an RGB color space to a YCbCr color space;

when each pixel point in the video to be processed satisfies Cb=Cr=0, determining the video to be processed as the grayscale pixel; or when each pixel point in the video to be processed does not satisfy Cb=Cr=0, determining that the video to be processed is the color pixel.

The present embodiment uses the color grayscale identification method of pix by pix to complete color grayscale pixel point identification in the unit of pixel points, and solves the problem of inaccurate area identification or limitation of area size in sub-area identification, and can satisfy the display application of any scene image.

The DICOM curve correction module 116 configured to, when the pixel type is a grayscale pixel, after the timing alignment module 115 executes delay processing, correct the video to be processed, so as to obtain a video to be output and output the video to be output.

For example: a pixel processed by the color grayscale pixel identification model, and if it is a grayscale pixel point, the timing alignment module processes a pipeline delay, and the number of delays is synchronized with the pipeline delay processed by the color pixel point, and is output to a post-stage processing module.

The brightness and chromatic aberration separation module 111 configured to, when the pixel type is a color pixel, separate the video to be processed, so as to obtain an initial brightness and an initial chromatic aberration of the video to be processed.

The GAMMA mapping processing module 112 configured to perform mapping processing based on a preconfigured mapping relationship and the initial brightness, so as to obtain a first RGB of the video to be processed in the GAMMA curve.

In the present embodiment, if it is a color pixel point, the brightness and chromatic aberration separation module separates the color pixel point into brightness and chromatic aberration parts, where the brightness is represented by L, and the chromatic aberration is represented by Rca, Gca and Bca respectively, and outputs same to a post-stage processing module.

In the present embodiment, the mapping relationship is:

$$D(x) = \frac{n}{m} G(x) + b;$$

where D(x) represents a correction function corresponding to the DICOM curve; G (x) represents a correction function corresponding to the GAMMA curve;

$$\frac{n}{m}$$

represents a mapping factor, the value range of $$\frac{n}{m}$$

is [0.9, 1.1], and n and m are positive integers; b represents a mapping brightness offset amount.

If the value of $$\frac{n}{m}$$

is too large or too small, the noisy points and color blocks will be caused to different degrees.

Where b is used as the mapping brightness offset amount, when the offset amount is increased, the brightness mapping relationship between the two curves can be corrected, and the range of b can be positive or negative.

When different DICOM and GAMMA curves are used, the above parameters can be used for fine-tuning the effect.

Where the GAMMA curve can include, but is not limited to: GAMMA1.8, GAMMA2.0, GAMMA2.2, GAMMA2.4, GAMMA2.6, etc.;

Where the DICOM curve can include, but is not limited to: DICOM300, DICOM400, DICOM500, DICOM600, DICOM700, etc.

By establishing the mapping relationship between the DICOM curve and the GAMMA curve, the brightness gradient between color pixels and grayscale pixels is reduced, thus the color grayscale transition part is smoother, and the problems of noisy points and color blocks are eliminated.

In the present embodiment, the GAMMA mapping processing module performs mapping processing based on a preconfigured mapping relationship and the initial brightness, so as to obtain a first RGB of the video to be processed in the GAMMA curve includes:

determining an RGB value corresponding to the initial brightness in the DICOM curve; and inputting an RGB value corresponding to the initial brightness in the DICOM curve into the mapping relationship for mapping processing, so as to obtain the first RGB of the video to be processed in the GAMMA curve.

The GAMMA chromatic aberration compensation module 113 is configured to compensating the first RGB based on the initial chromatic aberration, so as to obtain a second RGB.

In the present embodiment, the compensating, by the GAMMA chromatic aberration compensation module, the first RGB based on the initial chromatic aberration, so as to obtain a second RGB includes:

compensating the first RGB based on the initial chromatic aberration using the following formula:

$$\begin{bmatrix} R2 \\ G2 \\ B2 \end{bmatrix} = \begin{bmatrix} k1 & 0 & 0 \\ 0 & k2 & 0 \\ 0 & 0 & k3 \end{bmatrix} \times \begin{bmatrix} Rca \\ Gca \\ Bca \end{bmatrix} + \begin{bmatrix} R1 \\ G1 \\ B1 \end{bmatrix}$$

where $$\begin{bmatrix} R2 \\ G2 \\ B2 \end{bmatrix}$$

represents an RGB matrix corresponding to the second RGB, and $$\begin{bmatrix} Rca \\ Gca \\ Bca \end{bmatrix}$$

represents an RGB matrix corresponding to the initial chromatic aberration;

$$\begin{bmatrix} R1 \\ G1 \\ B1 \end{bmatrix}$$

represents an RGB matrix corresponding to the first RGB, $$\begin{bmatrix} k1 & 0 & 0 \\ 0 & k2 & 0 \\ 0 & 0 & k3 \end{bmatrix}$$

represents a chromatic aberration compensation coefficient matrix, k1, k2, and k3 respectively represent a chromatic aberration compensation coefficient, and the value ranges of k1, k2, and k3 are [0,2].

Where k1, k2, and k3 are used as the chromatic aberration compensation coefficient, different values can be taken for different chromatic aberration signals of RGB, k1, k2, and k3 are used for adjusting the chroma effect of color pixel points, which can meet the requirements of different users on chroma effects.

The chroma effects of the color pixel point GAMMA can be preserved by chromatic aberration compensation.

The DICOM mapping processing module 114 is configured to perform mapping processing on the basis of the mapping relationship and the second RGB, so as to obtain a third RGB of the video to be processed in the DICOM curve.

In the present embodiment, the way the DICOM mapping processing module performs mapping processing based on the mapping relationship and the second RGB is equivalent to an inverse process in which the GAMMA mapping processing module performs mapping processing based on a preconfigured mapping relationship and the initial brightness, which will not be described in detail herein.

The DICOM curve correction module 116 is further configured to perform correction based on the third RGB, so as to obtain the video to be output and output the video to be output.

In the present embodiment, the DICOM curve correction module performs correction based on the third RGB, so as to obtain the video to be output, including:

- acquiring a Look-Up-Table (LUT) to display a look-up table;
- correcting the third RGB based on the LUT display look-up table, so as to obtain the video to be output.

In the present embodiment, the outputting the video to be output includes:

- transmitting the video to be output to a display apparatus connected to the image correction system based on an FPGA.

For example: the display apparatus may be a medical display in the field of color displays, a general display, various display terminals, etc. When the display needs different adaptive correction processing of GAMMA and DICOM for the color grayscale pixels in the same display image, it cannot be completed in a single Scaler chip, only the special function of differentiation can be completed through the hardware programmable features of FPGA. Therefore, the image correction method based on an FPGA in the present embodiment can be used, and then the grayscale and color image can be accurately displayed on a single display at the same time, and the display characteristics of the respective images are retained.

Specifically, the adaptive hybrid GAMMA display method is implemented by using FPGA pure hardware through the color grayscale adaptive correction processing based on an FPGA, which can automatically identify the color pixels and monochrome grayscale pixels in the displayed image. The monochromatic pixels is subjected to a DICOM curve correction processing; after the separation of brightness and chromatic aberration, GAMMA mapping processing, GAMMA chromatic aberration compensation processing, DICOM mapping processing, and finally DICOM curve correction processing can effectively solve the problem of excessive brightness gradient of the DICOM curve and the GAMMA curve at the same grayscale, make the color grayscale image transition part display uniform, while the color part retains the curve characteristics of GAMMA.

It can be seen from the above-mentioned technical solution that the present application can identify color grayscale attributes of a video by using functional modules of the FPGA and by taking pixel points as units, so as to solve the problem of area identification being inaccurate or an area size being limited in sub-region identification, thereby meeting display application of images in any scene. Color pixel points are further separated into brightness parts and chromatic aberration parts, and according to a mapping relationship between the DICOM curve and the GAMMA curve, the transition of a color and grayscale transition part is made uniform; chromatic aberration is further used for performing brightness compensation for a GAMMA curve, such that the grayscale brightness of the GAMMA curve of a color part is basically consistent with that of a DICOM curve, so as to reduce a brightness gradient between different image grayscales, thereby solving the problems of noisy points, color blocks and color spots, etc. being present in a transition area during image display; and at the same time, the color part keeps the characteristics of the GAMMA curve, and monochromatic grayscale pixel points are corrected by means of the DICOM curve, and adaptive correction of color grayscale video images is thus achieved on the basis of an FPGA.

Figure 7:
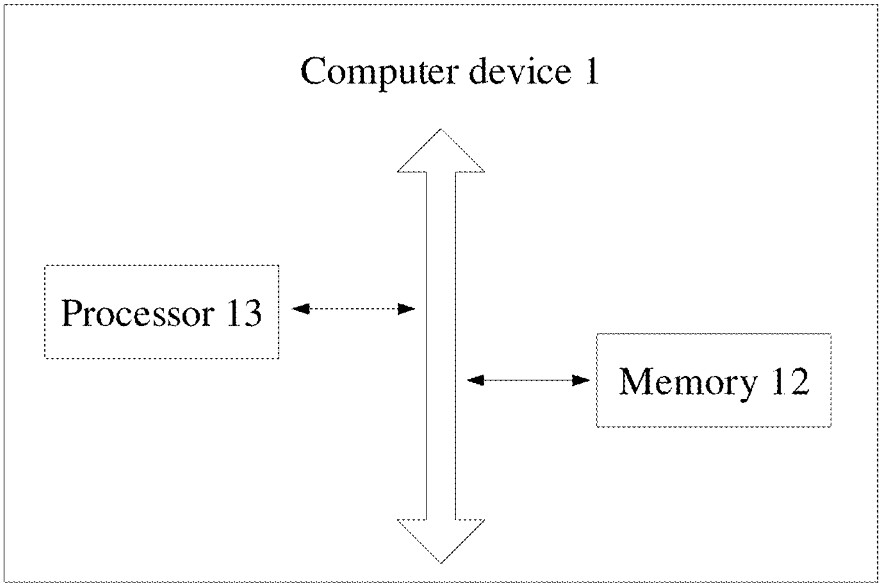
FIG. 7 is a schematic structural diagram showing a computer device implementing a preferred embodiment of an image correction method based on an FPGA according to the present application.

FIG. 7 shows a schematic structural diagram showing a computer device implementing a preferred embodiment of an image correction method based on an FPGA according to the present application.

The computer device 1 may include a memory 12, a processor 13 and a bus, and may further include a computer program, such as an image correction program based on an FPGA, stored in the memory 12 and executable on the processor 13.

It will be appreciated by a person skilled in the art that the diagram is merely an example of a computer device 1 and does not constitute a limitation of the computer device 1, that the computer device 1 may be either a bus-type structure or a star-type structure, that the computer device 1 may further include more or less other hardware or software than shown, or a different arrangement of components, e.g., the computer device 1 may further include input and output devices, network access devices, etc.

It should be noted that the computer device 1 described is only an example, and that other existing or future electronic products, such as may be adapted to the present application, are also included within the scope of the present application and are incorporated herein by reference.

The memory 12 includes at least one type of readable storage medium, where the readable storage medium includes a flash memory, a mobile hard disk, a multimedia card and a card-type memory (for example: SD or DX memory, etc.), magnetic memory, magnetic disk, optical disk, etc. The memory 12 may in some embodiments be an internal storage unit of the computer device 1, such as a mobile hard disk of the computer device 1. The memory 12 may in other embodiments also be an external storage device of the computer device 1, such as a plug-in mobile hard disk, a Smart Media Card (SMC), a Secure Digital (SD) card, a Flash Card, etc. provided on the computer device 1. Further, the memory 12 may include both an internal storage unit and an external storage device of the computer device 1. The memory 12 may be used not only for storing application software installed in the computer device 1 and various types of data, such as code of an image correction program based on an FPGA, but also for temporarily storing data that has been output or is to be output.

The processor 13 may in some embodiments consist of an integrated circuit, e.g., a single packaged integrated circuit, or a plurality of integrated circuits packaged with the same or different functions, including one or more Central Processing unit (CPU), microprocessors, digital processing chips, graphics processors, combinations of various control chips, etc. The processor 13 is the Control Unit of the computer device 1, connecting the various components of the whole computer device 1 with various interfaces and lines, by running or executing programs or modules stored in the memory 12 (e.g., executing image correction program based on an FPGA, etc.) and invoking data stored in the memory 12 to perform various functions of the computer device 1 and process data.

The processor 13 executes the operating system of the computer device 1 as well as applications installed. The processor 13 executes the application to implement the steps in the various embodiments of the image correction method based on an FPGA described above, such as the steps shown in FIG. 5.

Illustratively, the computer program may be partitioned into one or more modules/units that are stored in the memory 12 and executed by the processor 13 to implement the present application. The one or more modules/units may be a series of computer readable instruction segments capable of performing specific functions for describing the execution of the computer program in the computer device 1. For example, the computer program may be partitioned into a color grayscale pixel identification model 110, a brightness and chromatic aberration separation module 111, a GAMMA mapping processing module 112, a GAMMA chromatic aberration compensation module 113, a DICOM mapping processing module 114, a timing alignment module 115 and a DICOM curve correction module 116.

The integrated units described above, implemented in the form of software functional modules, may be stored in a computer-readable storage medium. The software function modules described above are stored in a storage medium including instructions to cause a computer device (which may be a personal computer, computer device, or network device, etc.) or processor to perform portions of the image correction method based on an FPGA according to various embodiments of the present application.

The integrated modules/units of the computer device 1, if implemented in the form of software functional units and sold or used as a stand-alone product, may be stored in a computer-readable storage medium. Based on this understanding, the present application implements all or part of the processes of the above-described embodiments, and may also be implemented by instructing associated hardware devices through a computer program, which may be stored in a computer-readable storage medium, that when executed by a processor, performs the steps of the various method embodiments described above.

The computer program includes, among other things, computer program code in the form of source code, object code, executable files or some intermediate form. The computer readable medium may include: any entity or apparatus, recording medium, U-disk, removable hard disk, magnetic disk, optical disk, computer ROM, read-Only Memory, random access memory, etc., capable of carrying the computer program code.

Further, the computer-readable storage medium may mainly include a storage program area and a storage data area, where the storage program area may store an operating system, an application program required for at least one function, etc.; the storage data area may store data created according to the use of a block chain node, etc.

The block chain referred to in the present application is a new application mode of computer technology, such as distributed data storage, point-to-point transmission, consensus mechanism and encryption algorithm. A blockchain, essentially a decentralized database, is a string of data blocks generated in association using cryptographic methods, each data block containing information about a batch of network transactions for verifying the validity of the information (anti-counterfeiting) and generating the next block. The block chain may include a block chain underlying platform, a platform product service layer, and an application service layer, etc.

The bus may be a peripheral component interconnect (PCI) bus or an extended industry standard architecture (EISA) bus, etc. The bus may be divided into an address bus, a data bus, a control bus, etc. For ease of illustration, only one straight line is shown in FIG. 7, but only one bus or one type of bus is not shown. The bus is arranged to enable connection communication between the memory 12 and at least one processor 13 etc.

Although not shown, the computer device 1 may further include a power supply, such as a battery, for powering the various components, preferably the power supply may be logically connected to the at least one processor 13 via power management apparatus, such that charging management, discharging management, and power consumption management functions are performed via the power management apparatus. The power supply may also include one or more of a DC or AC power source, a recharging apparatus, a power failure detection circuit, a power converter or inverter, a power status indicator, and any other component. The computer device 1 may also include various sensors, bluetooth modules, Wi-Fi modules, etc. which will not be described in more detail here.

Further, the computer device 1 may also include a network interface, which may Alternatively include a wired interface and/or a wireless interface (such as a WI-FI interface, a Bluetooth interface, etc.), typically for establishing a communication connection between the computer device 1 and other computer devices.

Alternatively, the computer device 1 may further include a user interface, which may be a Display, an input unit, such as a Keyboard, alternatively, a standard wired interface, a wireless interface. Alternatively, in some embodiments, the display may be an LED display, a liquid crystal display, a touch-sensitive liquid crystal display, an Organic Light-Emitting Diode (OLED) touchpad, etc. The display may also suitably be called a display screen or a display unit for displaying information processed in the computer device 1 and for displaying a visualized user interface.

It should be understood that the examples are for illustrative purposes only and are not to be construed as limiting the scope of the patent application.

FIG. 7 only shows a computer device 1 with components 12-13, and it can be understood by a person skilled in the art that the structure shown in FIG. 7 does not constitute a limitation of the computer device 1, and may include fewer or more components than shown, or combine certain components, or a different arrangement of components.

In connection with FIG. 5, the memory 12 in the computer device 1 stores a plurality of instructions to implement an image correction method based on an FPGA, and the processor 13 can execute the plurality of instructions to implement:

when a video to be processed is received, the color grayscale pixel identification model identifies the pixel type of the video to be processed;

when the pixel type is a grayscale pixel, after a timing alignment module executes delay processing, correcting, by a DICOM curve correction module, the video to be processed, so as to obtain a video to be output and then outputs same;

when the pixel type is a color pixel, performing separation, by a brightness and chromatic aberration separation module, on the video to be processed, so as to obtain initial brightness and initial chromatic aberration of the video to be processed; performing mapping processing, by a GAMMA mapping processing module, on the basis of a preconfigured mapping relationship and the initial brightness, so as to obtain a first RGB, of the video to be processed, in the GAMMA curve; compensating, by a GAMMA chromatic aberration compensation module, for the first RGB on the basis of the initial chromatic aberration, so as to obtain a second RGB; performing mapping processing, by a DICOM mapping processing module, on the basis of the mapping relationship and the second RGB, so as to obtain a third RGB, of the video to be processed, in the DICOM curve; and performing, by a DICOM curve correction module, correction on the basis of the third RGB, so as to obtain a video to be output and then outputs same In particular, the specific implementation of the above-mentioned instructions by the processor 13 can be described with reference to the relevant steps in the corresponding embodiment of FIG. 5, which will not be repeated here.

It should be noted that all the data involved in this case are obtained legally.

In the several embodiments provided herein, it should be understood that the disclosed systems, apparatuses, and methods may be implemented in other ways. For example, the apparatus embodiments described above are merely illustrative, e.g., the partitioning of the modules is merely a logical function partitioning, and additional partitioning may be practical to implement.

The present application is operational with numerous general purpose or special purpose computer system environments or configurations. For example: personal computers, server computers, hand-held or portable devices, tablet-type devices, multiprocessor systems, microprocessor-based systems, set top boxes, programmable consumer electronics, network PCs, minicomputers, mainframe computers, distributed computing environments that include any of the above systems or devices, etc. The present application may be described in the general context of computer-executable instructions, such as program modules, being executed by a computer. Generally, program modules include routines, programs, objects, components, data structures, etc. that perform particular tasks or implement particular abstract data types. The present application may also be practiced in distributed computing environments where tasks are performed by remote processing devices that are linked through a communications network. In a distributed computing environment, program modules may be located in both local and remote computer storage media including storage devices.

The modules illustrated as separate components may or may not be physically separated, the components shown as modules may or may not be physical units, i.e., may be located in one place, or may also be distributed over a plurality of network elements. Some or all the modules may be selected to achieve the objectives of the embodiments according to actual needs.

In addition, various functional modules in various embodiments of the present application may be integrated in one processing unit, may be physically present in separate units, or may be integrated in one unit in two or more units. The above-mentioned integrated units can be realized in the form of hardware or in the form of hardware plus software functional modules.

It will be evident to a person skilled in the art that the present application is not limited to the details of the foregoing illustrative embodiments, and that the present application may be embodied in other specific forms without departing from the spirit or essential characteristics thereof.

The present embodiments are therefore to be considered in all respects as illustrative and not restrictive, the scope of the present application being indicated by the appended claims rather than by the foregoing description, and all changes which come within the meaning and range of equivalency of the claims are therefore intended to be embraced therein. Any reference signs in the claims shall not be construed as limiting the claim concerned.

Furthermore, it will be understood that the word "include" does not exclude other elements or steps and the singular does not exclude the plural. Multiple units or means recited in the present application may also be implemented by one unit or apparatus by software or hardware. The terms first, second, etc. are used to refer to names and do not denote any particular order.

Finally, it should be noted that the above-mentioned embodiments illustrate rather than limit the present application, and that a person skilled in the art will appreciate that modifications and equivalents may be made thereto without departing from the spirit and scope of the present application.

The invention claimed is:

1. An image correction method based on a Field Programmable Gate Array (FPGA), wherein the image correction method based on an FPGA is applied to an image correction system based on an FPGA, the image correction system based on an FPGA comprising a color grayscale pixel identification module, a brightness and chromatic aberration separation module, a GAMMA mapping processing module, a GAMMA chromatic aberration compensation module, a DICOM mapping processing module, a timing alignment module and a DICOM curve correction module, and the image correction method based on an FPGA comprising:

when a video to be processed is received, identifying, by the color grayscale pixel identification module, a pixel type of the video to be processed;

when the pixel type is a grayscale pixel, after a timing alignment module executes delay processing, correcting, by a DICOM curve correction module, the video to be processed, so as to obtain a video to be output and then outputs same;

when the pixel type is a color pixel, performing separation, by a brightness and chromatic aberration separation module, on the video to be processed, so as to obtain initial brightness and initial chromatic aberration of the video to be processed; performing mapping processing, by a GAMMA mapping processing module, on a basis of a preconfigured mapping relationship and the initial brightness, so as to obtain a first RGB, of the video to be processed, in the GAMMA curve; compensating, by a GAMMA chromatic aberration compensation module, for the first RGB on a basis of the initial chromatic aberration, so as to obtain a second RGB; performing mapping processing, by a DICOM mapping processing module, on a basis of the mapping relationship and the second RGB, so as to obtain a third RGB, of the video to be processed, in the DICOM curve; and performing, by a DICOM curve correction module, correction on a basis of the third RGB, so as to obtain a video to be output and then outputs same.

2. The image correction method based on an FPGA according to claim 1, wherein the identifying, by a color grayscale pixel identification module, the pixel type of the video to be processed comprises:

acquiring an R value, a G value and a B value of each pixel point in the video to be processed;

acquiring a preconfigured component difference threshold;

calculating a component difference between the R value and the G value, a component difference between the G value and the B value and a component difference between the R value and the B value of each pixel point, so as to obtain a component difference corresponding to each pixel point;

when the component difference of each pixel point in the video to be processed is less than or equal to the component difference threshold, determining the video to be processed as the grayscale pixel; or when the component difference of each pixel point in the video to be processed is not all less than or equal to the component difference threshold, determining the video to be processed as the color pixel.

3. The image correction method based on an FPGA according to claim 1, wherein the identifying, by a color grayscale pixel identification model, the pixel type of the video to be processed comprises:

converting the video to be processed from an RGB color space to a YCbCr color space;

when each pixel point in the video to be processed satisfies Cb=Cr=0, determining the video to be processed as the grayscale pixel; or when each pixel point in the video to be processed does not satisfy Cb=Cr=0, determining that the video to be processed is the color pixel.

4. The image correction method based on an FPGA according to claim 1, wherein the mapping relationship is:

$$D(x) = \frac{n}{m}G(x) + b;$$

wherein D(x) represents a correction function corresponding to the DICOM curve; G (x) represents a correction function corresponding to the GAMMA curve;

$$\frac{n}{m}$$

represents a mapping factor, the value range of $$\frac{n}{m}$$

is [0.9, 1.1], and n and m are positive integers; b represents a mapping brightness offset amount;

the GAMMA mapping processing module performs mapping processing based on a preconfigured mapping relationship and the initial brightness, so as to obtain a first RGB of the video to be processed in the GAMMA curve comprises:

determining an RGB value corresponding to the initial brightness in the DICOM curve; and inputting an RGB value corresponding to the initial brightness in the DICOM curve into the mapping relationship for mapping processing, so as to obtain the first RGB of the video to be processed in the GAMMA curve.

5. The image correction method based on an FPGA according to claim 1, wherein the compensating, by the GAMMA chromatic aberration compensation module, the first RGB based on the initial chromatic aberration, so as to obtain a second RGB comprises:

compensating the first RGB based on the initial chromatic aberration using the following formula:

$$\begin{bmatrix} R2 \\ G2 \\ B2 \end{bmatrix} = \begin{bmatrix} k1 & 0 & 0 \\ 0 & k2 & 0 \\ 0 & 0 & k3 \end{bmatrix} \times \begin{bmatrix} Rca \\ Gca \\ Bca \end{bmatrix} + \begin{bmatrix} R1 \\ G1 \\ B1 \end{bmatrix}$$

wherein $$\begin{bmatrix} R2 \\ G2 \\ B2 \end{bmatrix}$$

represents an RGB matrix corresponding to the second RGB, and $$\begin{bmatrix} Rca \\ Gca \\ Bca \end{bmatrix}$$

represents an RGB matrix corresponding to the initial chromatic aberration;

$$\begin{bmatrix} R1 \\ G1 \\ B1 \end{bmatrix}$$

represents an RGB matrix corresponding to the first RGB, $$\begin{bmatrix} k1 & 0 & 0 \\ 0 & k2 & 0 \\ 0 & 0 & k3 \end{bmatrix}$$

represents a chromatic aberration compensation coefficient matrix, k1, k2, and k3 respectively represent a chromatic aberration compensation coefficient, and the value ranges of k1, k2, and k3 are [0, 2].

6. The image correction method based on an FPGA according to claim 1, wherein the DICOM curve correction module performing correction based on the third RGB to obtain the video to be output comprises:

acquiring an LUT display look-up table; and correcting the third RGB based on the LUT display look-up table, so as to obtain the video to be output.

7. The image correction method based on an FPGA according to claim 1, wherein the outputting the video to be output comprises:

transmitting the video to be output to a display apparatus connected to the image correction system based on an FPGA.

8. A computer device, comprising:

a memory storing at least one instruction; and a processor executing instructions stored in the memory to implement the image correction method based on an FPGA according to claim 1.

9. A computer device, comprising:

a memory storing at least one instruction; and a processor executing instructions stored in the memory to implement the image correction method based on an FPGA according to claim 2.

10. A computer device, comprising:

a memory storing at least one instruction; and a processor executing instructions stored in the memory to implement the image correction method based on an FPGA according to claim 3.

11. A computer device, comprising:

a memory storing at least one instruction; and a processor executing instructions stored in the memory to implement the image correction method based on an FPGA according to claim 4.

12. A computer device, comprising:

a memory storing at least one instruction; and a processor executing instructions stored in the memory to implement the image correction method based on an FPGA according to claim 5.

13. A computer device, comprising:

a memory storing at least one instruction; and a processor executing instructions stored in the memory to implement the image correction method based on an FPGA according to claim 6.

14. A computer device, comprising:

a memory storing at least one instruction; and a processor executing instructions stored in the memory to implement the image correction method based on an FPGA according to claim 7.

15. A non-transitory computer-readable storage medium, wherein the computer-readable storage medium has stored therein at least one instruction for execution by a processor in a computer device to implement the image correction method based on an FPGA according to claim 1.

16. A non-transitory computer-readable storage medium, wherein the computer-readable storage medium has stored therein at least one instruction for execution by a processor in a computer device to implement the image correction method based on an FPGA according to claim 2.

17. A non-transitory computer-readable storage medium, wherein the computer-readable storage medium has stored therein at least one instruction for execution by a processor in a computer device to implement the image correction method based on an FPGA according to claim 3.

18. A non-transitory computer-readable storage medium, wherein the computer-readable storage medium has stored therein at least one instruction for execution by a processor in a computer device to implement the image correction method based on an FPGA according to claim 4.

19. A non-transitory computer-readable storage medium, wherein the computer-readable storage medium has stored therein at least one instruction for execution by a processor in a computer device to implement the image correction method based on an FPGA according to claim 5.

20. A non-transitory computer-readable storage medium, wherein the computer-readable storage medium has stored therein at least one instruction for execution by a processor in a computer device to implement the image correction method based on an FPGA according to claim 6.

* * * * *